United States Patent [19]

Kass

[11] Patent Number: 4,500,509

[45] Date of Patent: * Feb. 19, 1985

[54] METACHROMATIC DYE SORPTION AND FLUORESCENT LIGHT EMMISIVE MEANS FOR DIFFERENTIAL DETERMINATION OF DEVELOPMENTAL STAGES OF NEUTROPHILIC GRANULOCYTIC CELLS AND OTHER LEUKOCYTES

[76] Inventor: Lawrence Kass, 3229 Sheatham Ct., Toledo, Ohio 43615

[*] Notice: The portion of the term of this patent subsequent to Aug. 23, 2000 has been disclaimed.

[21] Appl. No.: 356,578

[22] Filed: Mar. 9, 1982

Related U.S. Application Data

[63] Continuation-in-part of Ser. No. 242,662, Mar. 11, 1981, Pat. No. 4,400,370, which is a continuation-in-part of Ser. No. 129,680, Mar. 12, 1980.

[51] Int. Cl.³ .................. G01N 31/00; G01N 1/00
[52] U.S. Cl. ................................. 424/3; 424/7.1
[58] Field of Search .............. 424/3; 8/644, 657; 250/461.2

[56] References Cited

U.S. PATENT DOCUMENTS

| | | | |
|---|---|---|---|
| 2,126,852 | 8/1938 | Wolff. | |
| 3,560,135 | 2/1971 | Yamayo | 8/657 |
| 3,617,185 | 11/1971 | Drautz | 8/657 |
| 3,916,205 | 10/1975 | Kleinerman | 250/461 |
| 3,961,039 | 6/1976 | Sternheimer | 424/3 |
| 3,985,500 | 10/1976 | Streck | 8/657 |
| 4,146,604 | 3/1979 | Kleinerman | 424/3 |

FOREIGN PATENT DOCUMENTS 0004061 9/1970 European Pat. Off. .

OTHER PUBLICATIONS

Gurr, Synth. Dyes in Biol. Med. & Chem., Acd. Press, NY, 1971, pp. 54, 55, 90, 117, 147–149, 395, 805.
Conn's Biol. Stains, Williams & Wilkins, Baltimore, 9th ed., 1977, pp. 43, 368, 404–407, 415–428.
Gray, The Ency. of Microscop. & Microtech., Van Nostrand-Reinhold Co., N.Y., 1973, pp. 398–399, 469, 551, 563.
Humason, Animal Tissue Tech., W. H. Freeman & Co., San Francisco, 1972, pp. 128–132.
Hallberg, Acta Med. Scand., Suppl., vol. 180, 1946, pp. 7–15.
Pilot, Use of Base Fluids for Counting Eosinophils, U. of Ill., May 23, 1950, pp. 870–871.
Kodak Adv., Sci. Amer., May 1976, p. 49.
Ruddell, J. Invertebr. Pathol., vol. 31, 1978, pp. 313–323.
Williams, J. of Lab. & Clin. Med., vol. VIII, Oct. 1922–Sep. 1923, pp. 250–253.
Ruddell, Chem. Abs., vol. 89, 1978, Ab. No. 89:54252q; Chem. Sub. Index, p. 2791cs.
Simpson, Stain Tech., vol. 45, No. 5, 1970, pp. 221–223.
MacConaill, Ireland J. Med. Sci., Jun. 1964, pp. 243–250.
Sabin, Bull. Johns Hopkins U., vol. XXXIV, No. 391, Sep. 1923, pp. 277–288.
Spiridonovitch, The Anatomical Record, vol. 26, Jan.–May 1924, pp. 367–373.
Moore, PSEBM, vol. 82, 1953, pp. 601–603.

*Primary Examiner*—Robert J. Warden
*Assistant Examiner*—K. S. McCowin
*Attorney, Agent, or Firm*—Fay & Sharpe

[57] ABSTRACT

Differentiation, identification and enumeration of dye responsive human blood cells essential to diagnosis and prognosis of certain diseases is established by preparation of the reaction product of a human blood specimen of the patient in an aqueous fixative-free environment at blood temperatures with selected basic, cationic quaternary dyes, particularly basic orange #21. The so-prepared specimen becomes instantly responsive to emissive wave energy source exposure to stimulate reproducible fluorescent light emission from all of said dye responsive cells. The quantum of said fluorescent light energy emitted provides individual sets of data response relative to hue, value, chroma and intensity to permit differentiation, identification and enumeration of all of said dye responsive components in said blood specimen. By use of a bi-modal wave energy system involving additional use of white light wave energy absorbance, independent sets of data can provide both confirmatory and ancillary information.

13 Claims, 1 Drawing Figure

FIG. 1

METACHROMATIC DYE SORPTION AND FLUORESCENT LIGHT EMMISIVE MEANS FOR DIFFERENTIAL DETERMINATION OF DEVELOPMENTAL STAGES OF NEUTROPHILIC GRANULOCYTIC CELLS AND OTHER LEUKOCYTES

CROSS REFERENCE TO RELATED APPLICATIONS

This application is a continuation-in-part of U.S. application Ser. No. 242,662 filed Mar. 11, 1981, Pat. No. 4,400,370, entitled "Metachromatic Dye Sorption Means for Differential Determination of Developmental Stages of Neutrophilic Granulocytic Cells and Other Leukocytes" which in turn is a continuation-in-part of the patent application U.S. Ser. No. 129,680 filed Mar. 12, 1980, entitled "Individual Leukocyte Determination by Means of Differential Metachromatic Dye Sorption".

BACKGROUND OF THE INVENTION

1. Field of the Invention

In a parent application and a first continuation-in-part application thereof, discovery of a broad class of dyestuffs were disclosed which, under visible light range absorbance in a supravital blood analysis, provided notable advantage in the field of cytology.

This application is a continuation-in-part of U.S. Ser. 242,662 filed Mar. 11, 1981, and is related to the same subject matter as the first above Parent case which provides an improved method for optical differentiation of the five individual white blood cell species by use of a class of basic quaternary metachromatic dyes which were found to supravitally stain each of the species within a temperature range.

The subject matter of the first continuation-in-part application relates basically to a similar area of determination but is founded on the discovery that certain specific sub-classes of the dyestuffs broadly useful for differentiation, identification and enumeration of human blood cell leukocytes were also singularly useful as well in differential determination of developmental stages of neutrophilic granulocytic cells. The foregoing inventions were reduced to practice using light waves of the same wave length as present in ordinary daylight herein sometimes call white light spectrum.

Since reduction to practice of the first continuation-in-part application, U.S. Ser. 242,662 of Mar. 11, 1981, microscopic examinations of a supravitally dyed field has been made available which permits the observer to practice the general method of supravital human blood analyses as originally disclosed using "white" light (an electromagnetic energy form of radiation having a wave length of from about 4000 to 7700 angstroms), but now enlarged to include fluorescent light emissions. In the Parent and the Continuations white light spectra passing through the supravitally dyed specimen field is absorbed. Fluorescent light is related to light emissions and may be caused by the flow of some form of energy into the emitting body. Emission spectra of fluorescence results from the flow of energy being absorbed and light being emitted in characteristic frequency.

Fluorescent light emission for the purposes herein in the fluorescent microscope may be ultra-violet, violet and sometimes blue radiations. Mercury vapor light is commonly used. However, early experimentation points to the value of a single, coherent beam of light, as from laser technology, to be of use as well in some instances. It is known that in flow cytometry apparatus laser beams have been used to excite single cells exposed to acridine orange dye in cell sorters. Instruments can look at a single cell, determine its specific patterns and measure the intensity of the fluorescent colors. However, acridine orange has serious limitations being both pH and temperature dependant. Acridine orange does not exhibit useful metachromasia under an absorbtive light mode. Additionally, the dye tends to diffuse out and is not useful in supravital examination of (living) cells, e.g., it is concentration dependant. In the presently disclosed methods, laser light stimulation of prepared microscopic cells dyed with basic orange #21, for example, provides unique means for identification, differentiation and enumeration of blood cells and other tissues capable of manufacturing, transferring or storing blood cells. Laser light does not appear to excite or bring out a new quality of chromasia or interfere with metachromasia, so important a factor in the use of the dyestuffs of this invention. It can be focused with high power density within one cell making them more distinct and the measurement more precise. The colors emitted appear to be unchanged by the form of energy causing the sorbed dyes of this invention to fluoresce.

Using the specific groups of dyes herein disclosed and claimed, but particularly basic orange #21 which is unique with fluorescent means, and also as hereinbefore disclosed in the Parent case and the first Continuation-in-part also unique with white light absorbance, the art of cytology is immeasurably advanced.

Dyes originally disclosed in the Parent application have been broadly classed as methines, polymethines and cyanine dyes. Dyes broadly within the class include carbocyanines, merocyanines, azacyanines, oxanols, etc. However, so very few of this broad class have been found to be metachromatic and useful, particularly in the present field of use where they must also be metachromatic under fluorescent conditions as well as white light absorbance.

2. Description of the Prior Art

Ehrlich made biological elements more readily and easily recognized under microscopic examination and for photographic observation by use of dye stains (aniline dyes) to identify certain white blood cells. Ehrlich was the first to note that some dyes were metachromatic, observing that the staining of the cell or components such as granules of leukocytes causes the cell to take on a color different than that of the stain in solution or expected color from the stain. Basophils, for example, were observed to take on a color different from the stain. Other histological specimens other than blood cells have also been reported to stain in a plurality of identifiably different colors.

A review of the state of the art indicates it is almost universal practice, before staining (which presently uses a plurality of chemically differing dyestuffs in admixture) to employ a fixative procedure which may require up to an half hour treatment before the biological specimen is subjected to dye stain. Fixatives are generally preservatives and denaturants that often interfere with the sensitivity of the dye sorption. Illustratively, fixatives include formaldehyde both as liquid and vapor, absolute alcohols (methyl), picroformal, etc. Very often living cells do not stain using vital dyes and fixatives have been essential to staining the specimens. Cytochemistry includes considerable information on techniques developed to assure reproducible staining of blood cells. Many essential additives are normally unstable and deteriorate rapidly, thus making cellular identification difficult and in some instances unreliable. Dr. Thomas E. Necheles has observed in relation to leukocyte analysis that this "system has undergone little or no change in fifty years."

Dye staining does serve, however, as a means of discernment of otherwise undiscernable detail of conferring a color reaction on cells and their stainable components; metabolic, functional or pathological.

United States hospitals began leukocyte counting in the early 1900's, using the count as indicia as to whether emergency surgery was necessary, for example. In the U.S. alone, more than half a million differential counts are performed every day, most of them by manual methods. It is important that total white cell counts and differential cell counts be performed and reported without delay. Time is of essence and providing required analysis more rapidly is a desideratum.

The value of leukocyte counting having been established, the demand for rapid blood analysis has developed so that beginning about 1950 with the work of Mellors and Papincolaou (1952) development of automated differential leukocyte counting instrumentation means had developed into a plurality of intruments by 1980. The CYDAK unit was early used to investigate the feasability of blood cell classification which pointed up the importance of specialized staining procedures and features were extracted from optical density histograms of each cell image. The procedure established that cells could be differentiated into four of the five classes of leukocytes, namely; neutrophils, eosinophils, lymphocytes and monocytes. Young (1969) published results on an automated classification of five cell classes and Bacus in 1971 extended the differentiation.

However, it is understood that automated differential systems presently rely upon multiple dye usage and dye degradation systems or indirect fluorescent measurement using fluorescent dyes.

In the prior art staining of blood it has been observed that it is practice to use two or more stains in combination (Romanowski, Giemsa and Wright stains). These methods are difficult in practice to provide quality control. The methods require standardization in preparation of each dye stain component as well as in the method of specimen staining. In development of successful automated leukocyte counters, reproducibility of staining is even more important to verifiable analysis.

LARC stainer (used in commercial automated differential leukocyte counter) is reported (Mogler 1973) to be a mixture of some ten thiazine dyes, oesin Y and $2^1, 4^1, 5^1$ tribromofluorescein (P. N. Marshall). Present art stains most often are in fixative alcoholic solutions and employ two or more stains in combination. Accurate analysis of vital blood staining is made most difficult. With the difficulty presented in the controlled oxidation of methylene blue essential to Romanowski stains, for example, the problems of quality control of the added ten individually different dye stains as are used in combination become awesome.

It has been recognized in the art that the widespread standardization and adoption of a limited number of stains would ensure greater accuracy and reproducibility in cytological studies. Serious introduction of artifacts have been observed by use of fixatives and cause difficulty in interpretation and misinterpretation and leukocyte differentiation and enumeration. pH adjustments, heavy metal cations have been reported to prevent cytochemical tests from working in the expected manner. Some dyes, particularly azo dyes, are noted to demonstrate non-specific precipitation around cells; other degenerative changes in fixed blood samples include vacuoles, clover-leafing of nuclei, distortion cell shapes and smudges and interference with ideal staining. The importance of performing differential counts on as near living cells in the shortest possible time in order to obtain optimally useful and valuable blood cell analyses has been recognized. Alcoholic dye solutions interfere with supravital staining. So far as is known, freshly prepared water soluble stains exhibit a minimum denaturant effect upon supravital blood during examination. All dyestuffs are more or less toxic to the blood cells, but some are more so that others. It is material that the cells under examination remain living as long as possible. Rapidity of staining obviously shortens the exposure time, thus allowing greater opportunity to examine leukocyte cells before all vitality is lost. Automated differential leukocyte counting in less minutes is sought for.

Studies and review of the prior art of performing microscopic blood analyses and disease diagnosis has indicated it is not unusual for pathologists to warm the dye and the blood specimen to body temperatures (about 37° C.) before contact. Dr. Sabin had a "warm box" to insure temperature control.

It has also been noted that some dyes used in the prior art are quite temperature sensitive. The literature reports that cresylecht violet is not an operative stain above 30° C. It is considered important for the purposes of this method as disclosed herein that the dyestuff be useful to stain leukocytes at temperatures as high as 37° C. and no difficulty has been observed with the select dyes to temperatures of about 40° C.

In the Parent application, a relatively small number of metachromatic dyestuffs are disclosed as useful in identification of one or more species of leukocyte. Identification and differentiation was specifically related to polymophonuclear leukocytes (neutrophils), eosinophils, basophils, lymphocytes generally, and monocytes. A uniting commonality observed was that all of the dyes found to be operative for the purposes of the Parent application metachromatically stained monocytes differentially from others in the above group.

The unusual qualities of the dye basic orange #21 (CI #48035 and Spectral Curve 7) were observed in relation to the eosinophils, basophils, and monocytes, but as the B-cells are few in number they were initially overlooked. It was initially observed in the Parent case that optical differentiation between mature and immature neutrophils appeared potential in that the mature granules were different in chroma from the immature granules which were more red and orange in comparison. As this group, including myeloblasts, promyelocytes, myelocytes, metamyelocytes and bands are not always present in all blood specimens or present in significant numbers as is often the case with T-lymphocytes (or T-cells) and B-lymphocytes (or B-cells) they were not then all specifically identified as being metachromatically and differentially stained by basic orange #21.

Subsequent to completion of the work supportive of the Parent application, continuing research on the use of this unique dye in similar blood donor studies established that it was reproducibly possible. using this selected basic cationic dye of the methine. polymethine and quinoline class to distinguish through metachromatic response certain lymphocytes. It is also possible further to identify at least ten recognized granulocytes and lymphocytic cells established in the art to be of vital interest to the health sciences Platelets, also identified as thrombocytes, can also be identified and enumerated.

Further, this differentiation was immediate, it required no complex biochemistry or arduous pre-treatment of the blood specimens. Additionally, it was noted the dye exhibited minimum toxicity.

Micro spectrophotometric measurements were made with an aperture small enough to measure the color in the granules of supravitally stained leukocyte granulocytic cells. No other part of the cell entered into the measurements to any extent were found to provide extinction coefficients of the colors of the different leukocyte species which were consistently different and were often of an order of differences in hue, value or chroma of the order of 50 nanometers. These were recognizable peaks, consistent over many cells. It is understood that differences of the order of 5 nm are significant in microspectrophotometric measurements if the differences are consistent and reproducible.

Among the immature granulocytic cells immediately identifiable and distinguishable one from the other are myeloblasts and cells of the myeloid series, namely; promyelocytes, myelocytes and metamyelocytes. These are believed to be and are generally understood to be precursors of the polymorphonuclear leukocytes or neutrophils, which are also stained metachromatically so as to be readily and easily distinguished, identified and enumerated by the supravital blood analyses made possible by the advances disclosed herein.

As disclosed in the parent application, it is also practical at the same time to distinguish neutrophils, eosinophils, basophils, lymphocytes and monocytes from each other and from the foregoing precursors should they all be present in a specific blood sample under microspectrophotometric analyses.

Additionally, it has also been found that this unique dye provides an optically different pattern of color as well as a different density of each color of granule in bands, neutrophils and leukocytes. Thus, this quality of leukocyte cell can also be uniquely separated by optical differentiation from the other immature cells identified above. The differentiations in color, color arrangement and color density are also of such a degree of magnitude of difference that both human counting manually of all the above individually named cells can be accomplished, both with white light spectra (absorption) and fluorescence (emission).

Sources of fluorescent emission energies are, for example; mercury vapor lights, tungsten-halogen sources, lasers, deuterium sources, zenon, etc.

Evidence available also indicates automatic differential counting equipment will develop based upon and to be accommodated by differences due to the presence or absence of color and the physical patterns established in the nucleus and by the relative number, size, arrangement or pattern and hue, value and chroma (color) and color density due to the number of granules in the cytoplasm. The duality of colors under bimodal light exposures provides a double check on observation and a means of discovery of differentials in cell structure.

Almost unbelievably, but also demonstrated in the basic research thus far completed, is the further ability to differentiate B-lymphocytes or B-cells from T-lymphocytes or T-cells. Again, it is possible to spectrally identify each of these important lymphocytes, one from the other, qualitatively and quantitatively using the same dyestuff in the same supravital, fixative free analysis as well as to distinguish and enumerate immature and mature cells including bands. T-lymphocytes have been observed and identified in lymph node tissues and other tissues associated with white blood cell metabolism by means of the fluorescent mode of observation.

Earlier discovery of the capacity of basic organe #21 to differentiate, in addition to those cells disclosed in the Parent application, myeloblasts and blood cells of the myeloid series as well as bands and T-lymphocytes and B-lymphocytes extends the original potential field of usefulness of the dye unexpectedly beyond the capacity recognized in the Parent application. Supravital blood specimen fractions of fluids associated with healthy tissue or tissue suspected of abnormality such as plasma, lymph, serum, etc., containing one or more of the above cells after metachromatic staining may be examined microscopically under this bi-modal energy system herein described, or by use of either light source alone and thus differentiate each species of cell indicated above permitting enumeration and comparative study.

The present advance in the art, coupled with the parent disclosure establishes unparalleled advance in hematology, cytology and immunology and the ability to plan and conduct researches in an unlimited area of human health. Need for costly reactants, invaluable research time and more accurate data assembly have been thereby measurably advanced.

The art of diagnosis of disease has a new horizon beyond the present limits with the finding of fluorescent responses using a limited few of the basic quaternary cationic chemical class that has produced the unique dyes of this disclosure.

Initial observations made frist in the parent application (U.S. Ser. 129,680, filed Mar. 12, 1980) using a Zeiss fluorescent microscope revealed that carbocyanine K-5, a methine-polymethine class of dye, to be metachromatic both under white light absorbance and emitted fluorescence. Later examination of a large group of dyes within the above chromophore classification including reds and violets (listed below) and basic orange 21 all were found to supravitally dye monocytes to exhibit this dually metachromatic or bi-modal light response under the Zeiss fluorescent microscope.

Pursuing observation that basic orange #21 had shown not only metachromasia under white light spectra, but also under conditions of fluorescence stimulated continued research establishing that basic orange #21 is operable under fluorescent light sources to produce substantially the same patterns of cell geometry and arrangement in the same cells as were disclosed in the Continuation-in-part identification above. However, the fluorescent colors were not of the same color response as with white light sources, though the geometric patterns were entirely corraborated. Parallel examinations of the same prepared slide in a large number of instances of both normal leukocytes and those of patients with various stages of diseased conditions both under normal white light wave lengths, as was the subject matter of the parent application (U.S. Ser. No. 129,680), and under fluorescent light, as here, produced a remarkable demonstration of repeated leukocyte identifications and confirmations under both white light wave lengths and under fluorescent light wave lengths but with identifying colors of both different in bi-modal means of observation in hue, value and chroma and of varying visible light intensity, as well.

Studies carried forward using species of methine and polymethine dyes in leukocyte cell identifications continued to confirm unusual properties of certain dyes in this class, particularly basic orange #21, basic red #13, basic red #36, basic red #49, basic violet #7,15, #16, #36, #39 and #40. All of the just identified dyes were found to be metachromatic under white light wave lengths and under fluorescent emission and all instantly stained monocytes characteristically and metachromatically under the bi-modal means here described. Further tests determined that all of the foregoing dyestuffs were quite unusual in that they are also metachromatic in conjunction with certain biological specimens under fluorescent light and were also metachromatically fluorescent when used as supravital to stain monocytes.

Samples of dyes located in a world-wide search total about 2,000 in number and have been subjected to testing. Many of these dyes are no longer available from or through known dye sources.

Specific studies of basic orange #21 further reveal it to be unique among the dyes numbered above. Basic orange #21 is the only dye presently known which exhibits a bi-modal function for identification of all the biological blood cells named below. This unique dye functions under both white light spectrum and fluorescent light spectrum stimuli in a metachromatically different identification of each individual ones of the following leukocytes including the developmental stages of neutrophilic, granulocytic cells. Rapid supravital staining with aqueous solutions of basic orange #21 makes possible optical differentiation, identification and enumeration under fluorescent light spectra, for each one of the following cells; that is, with one prepared microscopic field and with either manual, sequential or simultaneous examination stereo-optical devices under white light spectra and fluorescent spectra stimulus. Two different but characteristically distinctive color patterns become available and each can be checked against the other to confirm identification of neutrophils, eosinophils, basophils, monocytes, lymphocytes, promyelocytes, myelocytes, metamyelocytes, bands and B-cells as well as T-cells! Time has not permitted exhaustive study of possible limitations of more advanced computer operated high technology devices where simultaneous readings of bi-ocular screens image both white and fluorescent light projections from a single specimen field as possible.

Optical devices are known which permit both simultaneous and sequential bi-modal analyses of apparatus useful for simultaneous measurement of absorption and fluorescence. (See page 144, J. Membrane Biology 33, 141-183 [1977] ©. Springer-Verlag, New York, Inc., 1977). Thus it is not unknown to subject a dyed biological specimen to observation under the stimulus of a bi-modal light source.

It is further a matter of record that fluorescence alone is often an easier, faster and more versatile light source in stimulating microscopic differentiation, but it is also known that this light source may introduce complications in calibration and accuracy due to artifact vulnerability. However, by making possible sequential use of both white light wave length and fluorescent light wave length in a comparative observation of a single biological test specimen dyed with a dyestuff that is not only metachromatic under white light spectra but metachromatic under fluorescent light spectra makes possible observation of both similarities and differences existant in the characteristic known components of leukocytes as to their nuclei primary granules, secondary granules, etc. Unique aspects of cell structure of eosinophils have been observed which assist in their differentiation, identification and enumeration.

The granules of eosinophils specifically show strong fluorescence only around the periphery of the granule in a "case" or "shell" pattern. As far as ascertained, this border or peripheral fluorescent pattern or shell uniquely identifies eosinophils. Such a structural indicia of a blood cell has not heretofor been known to have been described. The observation suggests that white blood cells are releated tissues upon further comparative studies under both fluorescence and white light spectra will be found to reveal further avenues of discovery and stimulate novel studies through newly observed apparent structural differentiation not even suspected to exist heretofore.

Another illustration of promise is a noted difference in the degree of intensity of nuclear fluorescence among various T-cells (T-lymphocytes). It is anticipated that these observed differences in fluorescent light emission provide clues to identification of T-cell sub-sets, e.g. supressor and killer cells. While it is recognized that there is an observable significant difference in T-cells under bi-modal light illumination, the significance of the differences noted is not presently understood.

Present vital interest in immune studies suggest a locus of practical interest and application of the bimodal observations possible with the supravital analytical methods hereby introduced. Observations of leukocytes and their developmental stages and the recognition of structural differences of the biochemistry and biophysics through bimodal light observations will lead to deeper understanding of their order and the disorders of disease.

A study of the chemical structures of basic orange #21 and base orange #22 was conducted upon finding the first to be most unusual and the second inoperative for the purposes herein.

The only differences to be observed are that the indolyl radical of each basic orange varies only by a change in the methyl group from a 2 position in basic orange #21 to a 1 position in basic orange #22. The methyl group is substituted on a carbon in basic group #21 and on a nitrogen group in basic orange 22. The 2 position in basic orange #22 has a phenyl group in place of the methyl group of basic orange #21 at the 2 position in the structure.

Prior art references indicate that it was not unusual in supravital analyses to employ three concentrations of dye in three preparations of slides in such analyses as are an essential check on results. With basic orange #21, the color differentials are so separated and the colors so exceptionally vivid that one can readily distinguish primary from secondary granules, instantly, with one dye and one slide, and with either white light spectra or fluorescent light spectra.

SUMMARY OF THE INVENTION

The present invention advances the art of cytology by providing a single basic quaternary cationic organic dyestuff of the methine and polymethine series which is selectively metachromatically sorbed by one or more peripheral blood cell leukocytes which provides unusual improvement in identification and differentiation between immature and mature members of the various species of the myeloid series and the mature white blood cells under either or both white light absorbance or fluorescent light stimulus. Heretofore, cytochemical means and complex stains had to be used for blood cell differentiation, often requiring an hour or more of tedious preparation to prepare and microscopically analyze by differentiation and enumeration of a single species of known leukocytes.

In practice, it now is practical to differentially stain and identify with one single pure dye (others may be permissibly combined for specific studies) in a simple aqueous contact with a peripheral venous blood sample or fraction thereof, including leukocyte enriched specimens thereof, each one of the following species or types of precursor cells, white blood cells, platelets, tissues closely associated with blood cells, etc., may be accurately and readily identified. These species include myeloblasts, promyelocytes, myelocytes, metamyelocytes, bands, neutrophils, eosinophils, basophils, B-lymphocytes, T-lymphocytes and monocytes. Platelets can also be identified and counted, and also shown metachromasia in their granules.

Each of the above species of leukocytes when subjected to supravital analyses after treatment with basic orange #21, is differentiated under both white light spectra and fluorescent light spectra by an unusual metachromatic response of the cells to the dye and to the light source to which the prepared field is exposed.

Under the bi-modal light sources in each instance of quality of light souce employed, each one of the individual species of blood related cells recited can be differentiated from its neighbors, each species can be counted, the total count of any species present determined, each species can be studies as to its morphology, and many determinations made of great value to the health sciences.

Fundamentally, each of the above named white blood cells or leukocytes differentially sorb light, either white light or fluorescent light, from the same pure metachromatic dyestuff, depending upon the quality of the dye, the species of leukocyte, and the dye reception by elements of the specific cells present in the specimen fraction analyzed.

In the absence of fixatives, the basic dye of this invention is sorbed metachromatically so that each one class, type or species of leukocyte reflects a characteristic light spectra or color different from every other class, type or species of leukocyte present in the sample. The strikingly vivid metachromasia under both white light and fluorescent light of the single orange dyestuff of this invention is unique and remarkable. Each species of the series including myeloblasts, promyelocytes, myelocytes, metamyelocytes, bands, neutrophils, eosinophils, basophils, B-lymphocytes, T-lymphocytes and monocytes so sorbs the single metachromatic stain as to reflect a distinguishing light spectra or color in the visible light range and another and different distinguishing light spectra or color when exposed to a fluorescent light range. Combinations of the dyes of this invention in combinations of others of the same chemical class exhibiting similar metachromatic behavior under bimodal light sources is not precluded.

DETAILED DESCRIPTION OF THE INVENTION

This invention is a continuation-in-part of the parent application U.S. Ser. 129,680 filed Mar. 12, 1980, which was based upon the discovery of a group of unique metachromatic dyes which could be used singly, but oftentimes in combination, to identify and distinguish five species of white blood cells, namely; neutrophils, eosinophils, basophils, lymphocytes and monocytes, one from the other, when present in a human blood specimen. This specification is also a further continuation-in-part of U.S. Ser. 242,662 of Mar. 11, 1981.

This invention provides further development of the discovery of the capacity of the dye known as basic orange #21 which used alone in an aqueous medium using supravital blood analysis technique on a fixative-free specimen or fraction to stain in an unusual and distinctive metachromatic manner the previously identified series of human blood cells and platelets, but under fluorescent light.

This individual species identification each one from the other under fluorescent light reflects a remarkable order of differential.

Basic orange #21 is identified by the Color Index number 48035, by its chemical structures and the spectral curves which are part of the Parent cases and the public record.

While it is not intended to be bound by theory, it is well known that almost any foreign additive has a tendency to denature proteinaceous materials. Heretofore, use of fixatives in preparation of blood samples for staining has been universal practice. Experience has indicated that fixing interferes with the co-operation between the metachromaticity of the cell and the metachromatic quality of the dyes of this invention. Troublesome artifacts in the field are also avoided by the simple expedient of supravital, fixative free, specimen use using a supravital technique. By use of the bi-modal light source technique herein, identification of the individual cells hereinbefore identified can be checked out eliminating artifact confusion entirely.

In the practice of this invention, staining is sufficiently instantaneous so that at normal blood temperatures (37° C.) the cytologist does not have to wait or resort to fine cytochemistry practices before cell dye development occurs and spectral differentiation between the previously enumerated family members of leukocytes, before beginning his microscopic studies, either manually or by automated differential leukocyte counting systems.

Types of fixative free blood samples that can be used:
1. Anticoagulated (E.D.T.A., citrated, heparin) whole blood.
2. Suspensions of leukocytes obtained by dextran and/or gravity sedimentation of anticoagulated whole blood.
3. Samples of whole blood treated with hypotonic solution lyse red blood cells, leaving primarily white blood cells and platelets behind.
4. Samples of other body fluids, like spinal fluid or pleural or ascitic fluid, as well as samples of joint fluid where white blood cells are of interest.

The present invention does not specifically provide for an automatic differential leukocyte counting systems under either white light spectra or fluorescent light spectra. Such means of analysis have been under in-depth examination and may be near commercialization.

The College of American Pathologists Conference in Aspen, Colo., August 1975, has published a series of papers delivered at that time in a collection entitled "Differential Leukocyte Counting". These reports provide development and "State of the Art" interest in automatic differential blood cell counting computers. Attention is directed to U.S. Pat. Nos. 3,916,205 and 4,146,604 (Kleinerman) where certain fluorescent dyes are used in particular combinations for automatic differentiation of certain leukocytes and other blood cells based on fluorescent light response. These references are deemed pertinent to the subject matter and ends of this disclosure. It is to be additionally noted that Kleinerman relies upon cell fixation, customary in microscopic studies of leukocytes and appear to rely upon fluorescent dyes which are not required to be or are metachromatic as well as fluoroescently active in the presence of leukocyte cells.

The prior art indicates several levels of discrimination in the performance of leukocyte differential counting. Basic or primary is differentiation between polymorphonuclear cells and "mononuclear" cells. On an intermediate level, the differentiation of polymorphs into neutrophils, eosinphils and basophils and the separation of "mononuclear" between monocytes and lymphocytes is said to be possible in principle.

An apparent third level of difficulty involving differentiation of neutrophils into immature and mature forms and the division of lymphocytes into normal and reactive types was originally recognized and mentioned in the parent application. The present continuation-in-part application as far as is presently known provides the only method of differentiating and confirming by obervation, employing only one single pure dyestuff the blasts, myeloid series, bands, polymorphonuclear leukocytes (neutrophils), eosinophils, basophils, B-cells and T-cells as well as monocytes with a single dye and single specimen fraction and a selection of light sources, under both white light and/or fluorescent light stimuli.

The present state of the art in automated differential leukocyte counters is understood to be in an advanced state of development insofar as the use of white light and/or fluoroescent light and a simple aqueous dye is concerned. Manual differentials with preliminary complexity presently appear principally relied upon. Automated differential counters are understood to be of two general classes or groups: 1. pattern recognition systems and 2. cytochemical differentiation systems. It is understood that staining methods of the prior art have been used with greater or less success and machine operators can monitor the operation on a cell-by-cell basis.

Present cytochemical systems, while precise, have yet to develop satisfactory calibrators and require highly qualified operators. The advantages of being able to observe a single microscopic field under bi-modal light control would appear advantageous.

In a brief survey of the prior art fluorescent dye and fluorescent light source methods of the prior art, the following points are of record. 1. At least two light sources are essential including violet and ultraviolet light; 2. A third light source appears needed as well. 3. The system is understood to require a plurality of fluorescent dye stains to identify and differentiate the species of leukocyte. 4. The system requires alcohol-fixed blood smears. 5. The system requires staining times of the order of ten minutes and rinsing time of one minute followed by a drying procedure. 6. There appears to be a decreasing order of fluorescence intensity from (a) eosinophils to (b) neutrophils to (c) monocytes to (d) lymphocytes. (Basophils identification is not reported). 7. In a flow cytometer tube system, the blood cells are fixed with formaldehyde and stained with three different stains. 8. Detected leukocyte fluorescences are differentially counted and classified by means of ratios of fluorescent light. 9. One patentee discloses identification of only four of the five leukocyte species. 10. Three fluorescent dyestuffs are specified which must be combined to produce a "single dye" composition which combination of dyes appears essential to the operation or method, not merely advantageous.

In the parent application ordinary white light was used to illuminate the microscopic field which is an electromagnetic energy form of radiation having the capacity to cause the sensation of vision in light radiation of from about 4000 to 7700 angstroms wave length. In the Parent case the selected portion of the visible light spectra passing through the dye-leukocyte medium in the field was absorbed. The term "fluorescence" is understood to be related to emissivity. Fluorescence is believed to be caused by emission of electromagnetic radiation by the selective dye-leukocyte emitting and which emissions cease when the energy input ceases. Present experience indicates the source of electromagnetic energy causing metachromatic emissions from and differentiating the basic orange #21 leukocyte dyed cells as described herein is not critical. It may be of a mercury vapor lamp, as commonly used in fluorescent microscopes; or it has been found satisfactory functional when the energy form is a very selective beam as from a laser. The term "absorption" appears to be applied to white light spectra, and "fluorescence" in the case of the latter emissions.

The methods disclosed are based on a supravital technique. There is possible a continuous monitoring system in hospital diagnosis and treatment where continuous critical white blood cell observation directly on the patient would be a desired end such as within the potential of the bi-modal methods disclosed.

The term supravital stain and supravital staining does not preclude the possibility of continuous perfusion through a shunt circuit from the blood vessels of living organisms and continuous monitoring of all possible white blood cells as they are passed through a specialized by-pass tube for observation and count using a coherent laser light as the energy source for fluorescence of each individual blood cell as it is observed under cell cytometry and as it is individually illumined (or made emissive of fluorescent light) as it passes a point of focus in the microscopically enlarged field.

Based on limitations inherent in panoptically stained specimens, over the past several decades a number of cytochemical tests have been devised to more precisely distinguish one type of blood cell from another. In general these tests are designed to detect increased amount of one type of substance in a particular cell compared to another, or to detect a substance(s) within a characteristic cellular organelle in one cell compared to another. For example, activity of nonspecific esterase is unusually high in monocytes and this activity appears to be particularly sensitive to inhibition by sodium fluoride. Likewise, identification of granulocytic cells depend for the most part upon demonstration of properties of lysosomes. For these purposes, detection of myeloperoxidase and specific esterase activities have been useful as cytochemical tests. Lysosomal granules of eosinophils contain myeloperoxidase that is resistant to inhibition by sodium cyanide, and granules of basophils stain metachromatically with a variety of dyes, due in part to their high content of cationic substances like heparin.

As will be noted herein, monocytes show a non-staining nuclear reaction but are identified by cytoplasmic and granular color differentiation with a few other unusual dyes disclosed herein which are also metachromatic under both white light and fluorescent light.

The supravital stain technique utilizing living blood cells and their differential affinities for supravital staining of these cells with dilute aqueous fixative free dyes avoid artifacts that often occur with conventional fixatives. Using both white light and fluorescent light substantially eliminates the confusion caused by artifacts. The vital staining technique and bi-modal light sources provided herein define a more accurate reflection of cellular localization of the dye (e.g. lysosomes, fibrillar structures, nuclear chromatin) than use of one light quality alone. Continued experience with the basic orange #21 dye and improvements in the automated technology of differential blood cell counting under bi-modal light sources in conjunction with supravital fixative-free staining of peripheral blood leukocytes introduces a further important addition to the field of cytochemistry.

Figure 1:
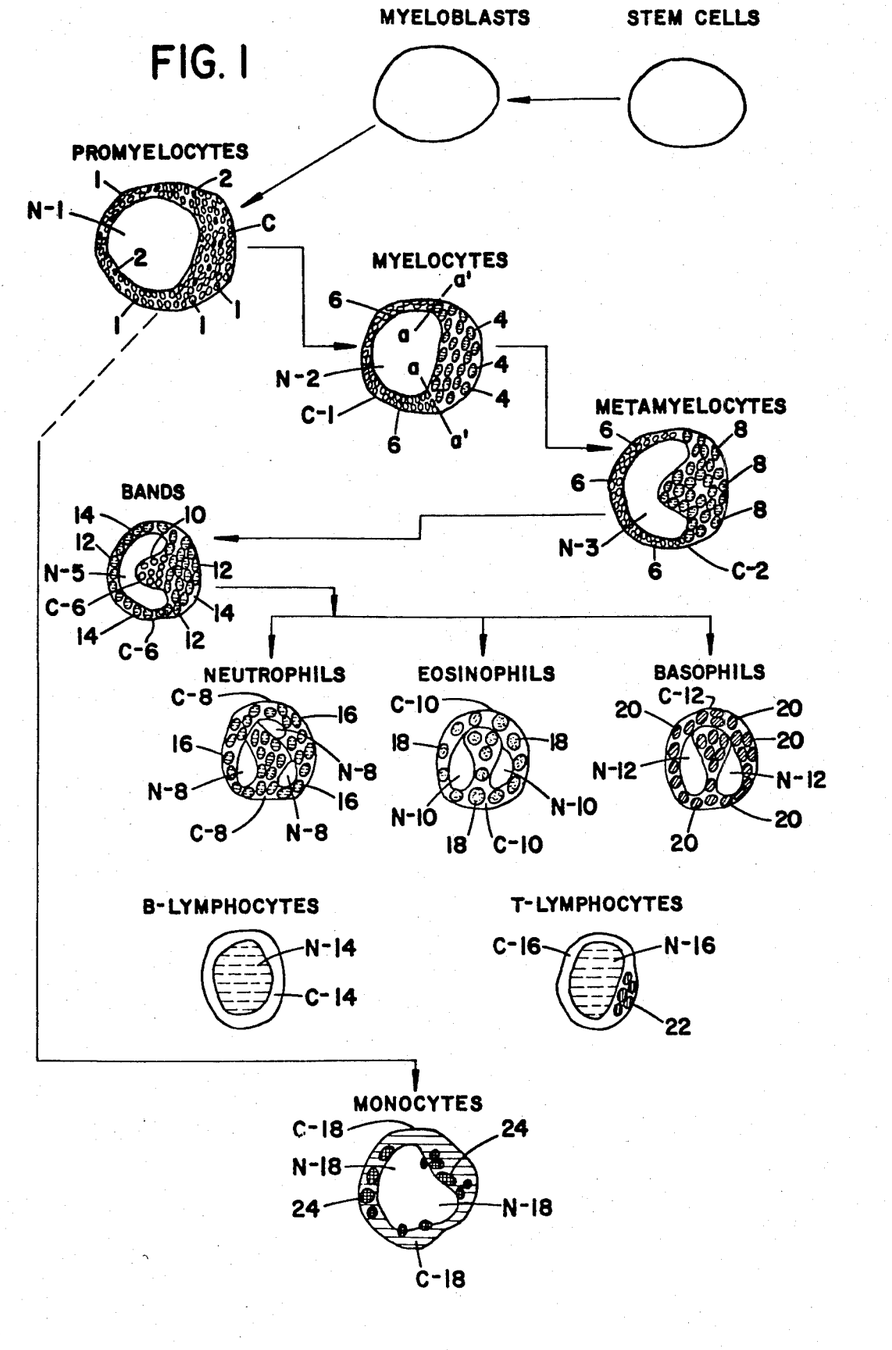

It is convenient at this point to refer to FIG. I as an aid in understanding leukocyte identification and differentiation as provided by the advance in the art herein.

Limitation to black and white illustration of FIG. I and the fact that the essential representations involve three dimensional objects and color variation and fluorescence all of which are identified only poorly by the grossness of language and black and white illustration and of limited spatial dimensions is an unfortunate loss of letters patent printed in black and white.

All blood cells appear to originate from undifferentiated stem cells called mesenchymal cells. Immediate descendants of the stem cells are called blasts, and the specific myeloblasts are understood to be progenitors of the leukocytes differentiated and made identifiable and enumeratable by their supravital analyses under either white light absorbance or fluorescent light emission or both, either simultaneously or sequentially when exposed to basic orange #21 in a fixative free aqueous environment. Myeloblasts are identified herein by the absence of granules or lysosomes which characteristically identify the three descendant cells of the myeloid series by their metachromatic color sorbtion or fluorescence. The three descendant cells, namely; promyelocytes, myelocytes and metamyelocytes are each separately identified by the metachromatic and differential color and color distribution as will be described.

Promyelocytes are readily identified by the following manual or automatic observations. They are generally largest in size of the myeloid series shown. The oval nucleus N-1 is not stained by basic orange #21 under absorbance nor by fluorescence and is relatively a larger part of the total granulocytic cell. Under absorbance the cytoplasm C is closely packed with large numbers of relatively small primary granules of an orange-red color (magenta) 1, and a few scattered violet granules 2 generally distributed amongst a large mass of orange-red primary granules. Under fluorescent emissivity the primary granules or lysosomes 1 fluoresce brightly yellow and the cytoplasm fluoresces a duller green.

Myelocytes also possess a non-stained ovate nucleus N-2 of slightly reduced area (volume). The outstanding distinguishing fact is the definite development in the myelocyte of larger secondary yellow granules 4 in a generally thickening crescent of the immature myelocyte cell. Dual imaginary lines a-a$^1$ bracket and delineate the increasing number of larger secondary yellow granules 4 of the myelocytes from the decreasing number of smaller orange-red or magenta primary granules 6. One can observe that myelocytes are distinguished from promyelocytes by the noticeable isolated component of developing secondary yellow granules 4. These absorbent (white light) magenta granules also fluoresce brightly yellow under fluorescent emissivity, and the developing secondary (larger) granules fluoresce a pale green.

Metamyelocytes like the two cells above ($N_1$ and $N_2$) also have a non-stained nucleus N-3 which begins to exhibit developing lobular pattern as distinct from the priorly described ovate form of the first cell in the myeloid series. The diminishing mass of smaller, primary, orange-red or magenta granules 6 now becomes a minor proportionate area of the total area of the observed cytoplasm C-2 of the cell. Larger secondary yellow granules 8 appear to displace a significant central portion of the previously ovate unstained nucleus N-3, which defines the change intended by the verbal expression—from ovate to lobular—. Fluorescent response patterns are consistently similar and recognizable. The secondary cells now have a larger size than in the myelocytes.

Bands are progressively distinctive and have been set apart from the first three cells described showing metachromatic staining of the granules and which are members of the myeloid series.

So far as presently known, bands have not been heretofore distinguished from all other leukocytes by the metachromasia of any dye.

Bands are distinguished from all other leukocytes by an unstained lobular formed nucleus N-5 which, along with the overall band size has noticeably decreased in area (volume) as compared with the prior leukocyte cells of the myeloid series. Additionally the lobular form of the unstained nucleus N-5 has become more bifurcated by further inward growth of the cytoplasm C-6. Growth by number increase of secondary yellow granules 12 in the cytoplasm has displaced all but a very small cluster of remaining primary, smaller, orange-red granules 10. Note that the cluster of red granules 10 are specifically located in the inward protrusion or movement of the cytoplasm C-6 tending to segment the nucleus N-5. Larger, secondary yellow granules 12 have succeeded to take over the cytoplasm C-6 except for this characteristic contrasting color group of bands. The important point of separation of bands is the small cluster of red granules 10 in cytoplasm C-6 at 10.

This outstanding point of differentiation of bands from all other leukocytes is suggested as extremely useful in development of automated equipment adapted to perceive the small primary orange-red granules 10 surrounded by a large preponderance of secondary yellow larger granules 12.

Like in absorbance, bands under fluorescence show a small cluster of yellow fluorescent granules 10 in cytoplasm C-6 in the above characteristic cell pattern with fluorescent pale green secondary granules 12 also preponderant.

Ability to easily, rapidly and certainly distinguish, identify and enumerate bands from all other leukocytes with but a single dyestuff under a bi-modal wave energy stimulus as described above is beyond expectation and beyond any known theory of band function.

Neutrophils are mature white blood cells and were known to be recognizable from the five main classes of white blood cells of interest in the Parent application. Further detail of interest has now been established.

Neutrophils, eosinophils and basophils, in the absence of color reproductions as in the drawings, are all of relatively similar physical configuration. Using basic orange #21 as the sole supravital dye in a fixative free environment, neutrophils are identified by secondary granules 16 in the cytoplasm C-8 which are mainly yellow. The nucleus N-8 is not stained and is generally segmented. The large secondary yellow granules 16 constitute the major area (mass) of the cytoplasm C-8. Under fluorescent stimulus the neutrophils are primarily identified, as above, by the characteristic tri-lobed (segmented) nucleus N-8 and the dull green fluorescence of the cytoplasm C-8.

Eosinophils under absorbed white light spectra also possess a segmented unstained N-10, but the large secondary granules 18 are differentiated from the neutrophils and basophils by their orange color which is the characterizing and main feature of the cytoplasm C-10.

Fluorescent excitation disclosed a most interesting and characterizing development with eosinophils. The general structure disclosing bisected nucleus N-10 is common with bi-modal light examination. However, the secondary granules show a bright yellow outline or "shell" fluorescence about the periphery of the secondary granules 18 which has not been heretofor recognized. This unique "marking" noted with eosinophils under emissive (fluorescent) stimulus provides a means of checking observations made under the earlier absorbance examination as well as suggesting a phenomena of interest as to the structure of the secondary granules themselves not known heretofor. Under both sources of energy input observation the general structures are otherwise confirmatory.

Basophils segmented nucleus N-12 is also unstained by basic orange #21 under absorbed white light spectra but the secondary granules 20 differ from the granules of the neutrophils 18 by metachromatically staining basophils granules 20 a bright crimson color having a faint blue tinge or undertone.

Fluorescent stimulus of the basophils also provides substantially a pattern structurally similar to that of absorbent light. However, the fluorescence of the secondary granules 20 provides an unusually brilliant lemon yellow fluorescent light emission therefrom.

Note in the indicated cell lineage that each of the leukocytes shown in the FIGURE, neutrophils, eosinophils and basophils actually are derived from their specific precursor bands. The FIGURE as drawn does not include this progression in detail. Promyelocytes are indicated as precursors of monocytes.

B-lymphocytes and T-lymphocytes have essential oval nuclei N-14 and N-16, respectively. Each of which nucleus N-14 and N-16 under absorbent light stains a similar yellow. The cytoplasm C-14 and C-16 in each case remains unstained. One characteristic of the cytoplasm C-16 of T-lymphocytes clearly differentiates T-lymphocytes from B-lymphocytes. This is the presence of the small cluster of red granules 22 in the cytoplasm C-16 of T-lymphocytes.

Observing the same specimens as above under the influence of a mercury vapor light source, as illustrative, the T-cells small cluster of granules 22 in the cytoplasm 16 fluoresce bright yellow and the nuclei N-16 have been observed to be most often substantially unstained but have been noted to exhibit a dull green fluorescence under the same examinations. The pattern under both methods of observation is quite comparative and confirmatory. In B-cells, the nucleus has been consistently a dull fluorescent green.

Observations under both qualities of energy stimulation, B-cells vary by a yellow color of the nucleus under absorption and a dull green fluorescence under emissive light conditions. In both aspects of bi-modal light energy examination there have been no cluster of secondary granules in the cytoplasms of B-cells observable. This pattern is decisive.

As noted in the Parent application, monocytes have been unusual in that under white light observation all of the dyes originally found metachromatically active of the basic quaternary dyes disclosed therein, and under the more recent studies utilizing fluorescent light emissive energies, monocytes have consistently acted both metachromatic as well as fluorescent, not only with basic orange #21, but with several other basic red and basic violet cyanine colors priorly disclosed herein.

With basic orange #21, the monocytes do not stain as to their generally ovate nucleus N-18. However, the cytoplasm C-18 acquires a pink cast in which are discernable a scattered, relatively small number of crimson and pink granules 24 differing in hue, value and chroma sufficiently from the "pink" cast of the cytoplasm C-18 to be clearly optically differentiated from cytoplasm C-18 which is of a generally similar pink coloration.

Under fluorescent electromagnetic wave energy stimulus, all the indicated members of the class of cyanine or methine and polymethine dyes referred to herein cause fluorescent emissions from so dyed monocytes. With basic orange #21, the few granules 24 in the cytoplasm C-18 are a bright fluorescent yellow. Named basic violets and basic reds that stain monocyte nuclei metachromatically by absorption also fluoresce metachromatically by emissive energy.

Identification and enumeration of monocytes has been simplified by discovery as also described in the parent application with the set of unusual dyes therein disclosed. The standard fluoride sensitive non-specific esterase reaction cytochemically used for monocyte identification often requres an hour or more to complete and requires accurate cytochemical manipulation to be successful. With any one of the disclosed dyes, the dyeing of buffy coat suspension, whole blood or separated fractions and examination can be performed simply, without chemical adjustments, in the order of minutes. Staining of monocytes by the present application method using only basic orange #21 is instantaneous as to the cytoplasm, and the granules in the cytoplasm.

It should be noted that the metachromatic dyes may ultimately stain cells to a point where bi-modal identification are lost. Thus, the color differences reported in this disclosure may be lost, or diminished to a great degree if analyses are not promptly performed. As practical staining occurs almost immediately in all known instances, no extended waiting period for maximum differentials is, however, necessary.

In the prior art identification and differentiation of monocytes has been accomplished by time-consuming and complex cytochemical treatment of the cells involving non-esterase reaction, fixed cell preparation, hexazotization, pH adjustment and dye staining with multiple dyestuffs requiring about sixty minutes to accomplish what can be done with any one of the dyes of the Parent application under either white light spectra or fluorescent spectra, if desired, in less than a minute by a simple dye and blood sample contact with an aqueous system. With the specific dye of the present process as herein disclosed, there is also instantaneous and preferential staining of the cytoplasm of monocytes.

The unique cyanine dyes named herein are prepared for the proposed end use and for the purposes of this invention in filtered aqueous solution at approximately 1% concentration of the pure basic orange #21, as illustrative, in distilled water. The dye concentration is not particularly critical but permits some variation. It is preferred that aqueous solutions be used while fresh and that toxic additives not be included. Interference with the metachromatic reaction between dyestuff and the specific type or class of leukocyte may be totally inhibited by the presence of any of the known classical fixatives.

The definitive language "supravital" as used herein is an important limitation. It is applied to the original blood sample and is applied to living cells freshly removed from a living organism, or one freshly sacrificed, or equivalent. As the term is used here it is intended to exclude all "fixatives" but permits use of anti-coagulants (heparin, E.D.T.A., etc.). The blood cells may also be removed from bone marrow, urine and other biological specimens containing them, including as illustrative, lymphatic tissue and spleen.

The general practice of this invention is illustrated by the following.

A 1% solution in distilled water is made up of the selected basic quaternary cationic dye. Filter off all non-dissolved solids. Most useful is basic orange #21. If practice indicates it necessary, one or more of the subject dyes can be blended together as aqueous solutions if for a specific end.

The aqueous solution of the selected, previously identified, single pure dye (or one can employ combinations of one or more of the pure dyes as are disclosed in Tables I and II, as illustrated in Table III of the Parent application) is solubilized to produce a simple aqueous dye solution. (Consideration of various volumetric proportions of the aqueous dye solution, and various strengths of aqueous dye solutions may provide optimum conditions for various specific cytological analyses.) Some experimentation may lead to specific combinations having particular advantage and is contemplated by but beyond the scope of this disclosure.

Blood samples may be made available from various sources but fresh samples of venous blood from which erythrocytes have been removed (centrifugation, hypotonic lysis, gravity sedimentation, density gradient sedimentation, etc.,) or the sample may be a plasma enriched with white blood cells by known physicochemical techniques have been principally used. Tissues having cells (as described above) present may also be dyed and subjected to bi-modal light stimulus for study.

It is preferred to combine the aqueous dye and blood sample, both as freshly prepared, at the temperature of normal blood or body (about 36°–40° C.) where favorable to the analyses planned. More rapid and sharper staining at the higher temperature is generally obtained. Basic orange #21 does not appear temperature sensitive.

Dye and blood solutions work well when combined volumetrically at a ratio of about 1:4. Gently agitate the mixture for several seconds and examine a drop of the mixture immediately as a wet mount using a glass coverslip under a light microscope or automated differential leukocyte counting device, if available. Other means of contact between the dye and blood cells including using known media, illustratively gelatin, emulsions, etc., impregnated with the dye at about 1% dye concentration. Fixing the sample seriously interferes with the unusual metachromatic co-action of the dyestuffs of this invention with the leukocytes.

Basic orange #21 dye makes possible examination under white light alone, under fluorescent light alone, or both either simultaneously, singularly or in sequence depending upon equipment available and to distinguish the following one from the other if they are present together: myeloblasts, promyelocytes, metamyelocytes, myelocytes, bands, neutrophils, eosinophils, basophils, B-lymphocytes, T-lymphocytes and monocytes. Outline of the means of differentiation for enumeration and other study have been priorly developed in the Figure. The foregoing technique aids in identification.

The examples included herein as illustrative will assist one skilled in the art to appreciate the potential of the novel methods proposed. Not the least of the advantages of the method(s) are leukocyte counts (total), leukocyte counts of species, diagnosis of diseases, particularly leukemias, and the monitoring of patients receiving a variety of critical treatments, illustratively, chemotherapy, radiation therapy, ACTH, etc.

Identification and enumeration of one, selections or all of the species of leukocytes is often critically important in diagnosis and treatment of disease.

The examples which follow the detailed description of the invention are intended to illustrate the utility of the invention and its practice. Obviously, they are not exhaustive nor are they to be considered limiting.

EXAMPLE 1

(Basic Orange #21)

[An extensive series of methine, polymethine, quinoid and/or carbocyanine dyes were obtained based upon the initial discovery that basic orange #21 was found to be unusually metachromatic in relation to differential staining of white blood cells. Only basic orange #21 of over 2000 dyestuffs was found to exhibit the unusual metachromasia under white light and fluorescence as herein illustrated.]

50 ml. of peripheral blood was obtained from normal individuals in a series of heparinized tubes.

Duplicate tubes were admixed with 10 ml. of a 1% solution of basic orange #21 dyestuff in distilled water at about 37° C. The temperature has not been observed to be critical with this dye use.

Under microscopic study eosinophils originally described as having brown granules are now more accurately described here as having large orange granules in the cytoplasm under absorbance and fluoresce a bright yellow in a shell pattern with a non-stained lobular nucleus under both lights. Basophils were bi-modally observed to have a similar geometric configuration, but the granules under absorbance were bright crimson in mass tone with a faint blue tinge and fluoresce a bright yellow. The nucleus was also lobular, and not stained under bi-modular examination. Monocytes were clearly differentiated by non-stained oval nucleus and a pink cytoplasm containing a few crimson and pink granules. Under fluorescent light the granules are bright yellow. Non-stained may include very pale casts depending somewhat on the elapsed time before reading the slide.

Quite remarkably, the differential staining of both mature and immature neutrophils was more specific than any dyestuff heretofore observed in our studies or reported elsewhere in the prior art. Under absorbance mature neutrophils were spectrally identifiable by the few mainly yellow larger granules in the cytoplasm and the lobate unstained nucleus. Under florescence, the cytoplasm was a dull green fluorescense and the granules were not as visible.

EXAMPLE 2

T-cell rich and B-cell rich suspensions of human blood were prepared from 50 ml. specimens of peripheral blood obtained from normal individuals in heparinized Vacutainer tubes by passage of Ficoll-Hypaque enriched fractions through micro-columns of nylon mesh gauze. T-cell rich and B-cell rich suspensions were eluted from the columns using controlled temperature conditions with selected different buffers as is known in the prior art.

Fractions of these recovered suspensions were subjected to immunologic analyses using T-cell rosetting for T-cells and surface immuno-globulin detection for B-cells. One drop of a 1% aqueous solution of basic orange #21 dye was incorporated into 5 drops of the recovered suspension in separate test tubes. Each tube contained approximately $2 \times 10^6$ lymphocytes. Lymphocytes identified as T-cells by virtue of T-cell rosette formation were microscopically observed under white light spectra to contain small groups or clusters of 5 to 10 or more red granules. Under the fluorescent mode, the nucleus in some instances were unstained, or a dull green fluorescence, and the same clusters of granules fluoresced a bright yellow. Lymphocytes identified as B-cells by immunological methods exhibited only a rare red stained granule in the cytoplasm, most of the B-lymphocytes had no red granules present in the cytoplasm. The nucleus was oval and under absorbance stained yellow in both T-cells and B-cells. Under the fluorescent mode the nuclei of B-lymphocytes were a dull fluorescent green and the cytoplasm was unaffected.

Use of basic orange #21 provides a new, rapid method for identifying, differentiating and counting T and B lymphocytes or cells bi-modally or under fluorescent stimulus alone. Present methods involve use of unstable biological reagents, (sheep cells), require radioisotopic techniques which are costly and time demanding, require control of many variables including temperature, pH of incubation media, etc., which no longer appear necessary.

EXAMPLE 3

A 48 year old woman patient terminally ill with breast cancer developed septicemia and a high fever shortly before death. At that crucial time her white blood cell count rose to 45,000 per mm$^3$. By use of the standard Wright's stain, it was established that 60% of the peripheral blood leukocytes were bands having a characteristic unsegmented nucleus.

Specimens of the patient's blood was stained with a 1% aqueous solution of basic orange #21 as a supravital stain without fixatives.

Bands were identified by the consistent presence of a small cluster of red staining (primary) granules amidst a larger number of larger (secondary) granules which were metachromatically stained yellow as well as the typical unsegmented nucleus. Fluorescent light caused the primary granules in the cluster to exhibit a yellow fluorescence.

Thus it was possible to make positive identification, differentiation and enumeration of the band forms on the basis of their cytoplasmic maturation and color differentiated primary vs. secondary granulation under absorbance, and the yellow fluorescence of the cluster of primary granules.

EXAMPLE 4

A 24 year old man developed fatigue, and was found on physical examination to have an enlarged spleen. Laboratory values included a white blood cell count of 15,000/mm$^3$, and approximately 75% of the cells were atypical lymphocytes. On further immunologic testing, these were found to be T-cells. The patient had a positive mono spot test, and the diagnosis of infectious mononucleosis was made. Using basic orange #21 as a supravital stain, most of the lymphocytes contained a cluster of metachromatically staining red granules in the cytoplasm very near the unstained nucleus. Using fluorescence, these same granules fluoresced bright yellow with a dull fluorescently green nucleus.

EXAMPLE 5

A 75 year old man developed enlarged lymph nodes in the neck and groin, as well as an enlarged spleen. Laboratory studies disclosed anemia, and white blood cell count of 80,000/mm$^3$. Approximately 90% of these cells were lymphocytes, and on bone marrow examination, the marrow was largely replaced by similar appearing lymphocytes. The diagnosis of chronic lymphocytic leukemia was made. On immunologic testing, the lymphocytes were B cells. Under white light using basic orange #21 as a supravital stain, no granules were seen. Using fluorescence, no granules could be visuallized in the cytoplasm of the lymphocytes.

EXAMPLE 6

A 33 year old man developed weakness and fatigue, and was found to have a markedly enlarged spleen. Laboratory examination revealed a white blood cell count of 800,000/mm$^3$ along with a mild anemia but a normal platelet count. On a standard Wright's stain of the peripheral blood, all stages of maturation of leukocytes were seen, with predominance of promyelocytes, myelocytes and metamyelocytes. Numerous eosinophils, basophils, and nucleated erythrocytes were seen. On the basis of bone marrow and cytogenetic evaluations, the diagnosis of chronic granulocytic leukemia was made.

With basic orange #21 used supravitally with white light, the expected metachromatic differentiation of leukocytes was seen. With fluorescent light, the primary granules that stained metachromatically red appeared as bright yellow to yellow green fluorescence. Cells that contained mainly secondary granules (e.g. neutrophils) showed bright yellow color using white light, but dull green fluorescence using fluorescent light. Basophils showed bright yellow fluorescence of their granules, and the same granules appeared bright red using white light. In eosinophils, the granules stained bright orange using white light, but using fluorescent light, the granules showed fluorescence only around their periphery, in a "shell" fluorescent pattern.

EXAMPLE 7

A 25 year old woman with bronchial asthma had a routine blood count as part of her physical examination. On the leukocyte differential, approximately 40% eosinophils were found. Using basic orange #21 supravitally with white light, the granules of eosinophils stained orange. Using fluorescent light, the same granules showed a "shell" fluorescence.

EXAMPLE 8

A 62 year old woman with diabetes mellitus and terminal carcinoma of the colon developed anemia and leukocytosis shortly before death. The white blood cell count was 35,000/mm$^3$, and on Wright's stain showed numerous myelocytes and promyelocytes. Using basic orange #21 as a supravital stain with white light, the metachromatically staining red or magenta colored granules of promyelocytes and myelocytes exhibited a bright yellow fluorescence. As expected, these granules were more numerous in promyelocytes than in myelocytes.

EXAMPLE 9

In a 47 year old male with acute lymphoblastic leukemia, the white blood cell count was 10,000/mm$^3$ containing 80% leukemic lymphoblasts (PAS positive and terminal deoxynucleatidyl transferase passive). With basic orange #21 used supravitally, these leukemic lymphoblasts showed faint yellow nuclear staining with white light, and little or no nuclear fluorescence using fluorescent light.

Leukemic blasts from several patients with acute leukemia show a substially diminished fluorescence compared to normal leukocytes. Thus differences between normal and leukemic cells are differentiated.

DEVELOPMENT OF THE INVENTION

In the foregoing specification and examples there has been emphasis on the importance of the advances here disclosed in application to automated differential leukocyte computing devices. It is not known presently that "off the shelf" commercial equipment is directly useful without some modification for advantageous use of the bi-modal light method herein disclosed or for sole use of fluorescent light which has been employed in the prior art.

It is known, however, that at least three pieces of analytical equipment based on emission of fluorescent light are available using, in some instances, prior art dyestuffs which are not metachromatically fluorescent in nature. It is understood these devises are capable of determining patterns of light illuminated cells, of determining sizes of special patterns defined by fluorescent color differences and that various coherent light lasers are used, in whole or in part, for identification and enumeration of so differentiated cells. Those known in the prior art include Epic V (Coulter), FACS (Becton-Dickinson) and Cytofluorograph (Ortho).

Those skilled in the art and working in the field of medical technology are aware of the importance of rapid, accurate determination of the various differential leukocyte counts for a variety of ends. It has been estimated that in the United States each day a half million differential leukocyte counts are performed, most of them by manual techniques at an annual cost of over 750 million dollars.

Such counts, whether manual or automated, have a fundamental requirement of identification, spectral differentiation, enumeration and diagnostic aid in practice of medicine. The foregoing advance in these fundamentals will no doubt give rise to advances in ancillary automated equipment as herein indicated.

Blood counts as are of concern herein, whether manual or automated, are vital aids in examination and determination of the nature of disease. Fevers of unexplained origin; whether viral or non-pyogenic infection, pyogenic involving appendix, gall-bladder, fallopian tubes; prognosis of patients with various diseases in various stages; malignancies including Hodgkins disease; pulmnonary disease; surveillance of patient treatment with adrenocortical steroids; various kinds of acute and chronic leukemias, differentiation in diagnosis, between aseptic infarction of bone and osteomyelitis; bacterial infections and many other medical questions are aided in diagnosis, prognosis and treatment by accurate leukocyte counting, analysis and cytological study.

As used herein, the term metachromatic has relation to not only to the peculiar and unusual quality of the dyestuffs disclosed but to the quality of the various components, illustratively nucleus and cytoplasm, of each of the individual species of leukocytes which metachromatically co-react with something akin to synergism to produce the differentiation in spectral response which makes the described advances in cytochemistry possible. In essence, each white blood cell species sorbs (or fails to sorb) a single metachromatic dyestuff in some unusual and unique manner so that each dye-sorbed cell reflects an individual and different light spectra under ordinary white light stimulus and absorbance and fluorescent emissions. Oddly the dyes herein disclosed are metachromatic under both white light and fluorescent emission.

It has been well known that certain granular leukocytes have different affinities for various dyes, that is, basophils have affinity for basic dyes, eosinophils have affinity for acid dyes and that neutrophils do not stain intensely with either acid or basic dyes, no morphological features or chemical behavior is suggested that makes possible the specificity of basic orange #21 in making such sharp distinctions as here found between T-lymphocytes and B-lymphocytes and the unusual distinction in bands, under bi-modal light stimulus as disclosed above.

This is the more arcane when it is found that basic orange #22, which varies as to its structural chemistry only in two secondary group position variations as discussed earlier, is totally inoperative for the uses as set out herein.

Identification, differentiation and enumeration of monocytes has valuable diagnostic significance. Increased numbers of monocytes in the blood may indicate the presence of active tuberculosis, septicemia or blood poisoning and lymphomas like Hodgkins disease in diagnosis. Increased number of monocytes in the blood of persons recovering from hypoplastic or aplastic anemia may herald a favorable prognosis for the patient. Rapid and accurate microscopic analyses of monocytes under two different types of light quality favors extended application of a valuable technique.

Detection, identification and enumeration of polymorphonuclear leukocytes (neutrophils) are critical parameters in all blood evaluations. They are especially vital in the diagnosis of acute infections like pneumonia or peritonitis where the number of neutrophils are increased. They are important in monitoring patients receiving chemotherapy and for radiation therapy. Decreased numbers can occur in overwhelming infection, as a manifestation of drug toxicity, hyperactivity of the spleen and in acute leukemia.

If the absolute neutrophil count falls below 1000 mm$^3$, the risk of infection increases sharply. The specific dye of this invention instantly stains the granules or lysosomes which are characteristic identifying structures of polymorphonuclear leukocytes or neutrophils under either one or both described light sources.

Eosinophils are involved in allergic reactions, as are the basophils. Lymphocytes are involved in inflammation and to a greater extent in immune reactions and response to antigens (foreign bodies). Eosinophils are here instantly identified by the large orange granules in the cytoplasm, and the lobular configuration of the unstained nucleus under light absorption and the unusual shell fluorescence when the dyed blood or tissue specimen is stimulated to fluoresce.

Eosinophil counts are used in following the medical administration of adrenocorticotrophic hormone ACTH in the treatment of clinical conditions. Prior methods introduced confusing artifacts and indefinite forms confusingly similar to the eosinophils. Accuracy of the blood cell count with the prior art decreases with the time between blood sample preparation and completion of the count. Multiple dyes are essentially used. Acid and base staining is often required. The prior art dyes used tend to crystallize out of solution on standing.

Lymphocytes, specifically identifiable as a class with blue borrel, are known to be related to inflammation and immunity. They are increased in number in the blood of persons with chronic lymphatic leukemia and in persons with pertussis (whooping cough). The count may be decreased in patients undergoing chemotherapy and radiotherapy, in patients with lymphoma and various types of hereditary immunological deficiencies.

Basophils have a cytoplasm which contains large granules that are rich in cationic substances like heparin, serotonin and histamine. They are involved, for example, in allergic reactions.

The principal advance in this continuation-in-part application has been the discovery that there is presently one unique dye which differentially stains lymphocytes, previously stained only as a class by blue borrel at lower temperatures which can be used in a single pure form for both manual and automatic identification and under both white light spectra and fluorescent spectra to give two modes of checking out a given microscopic cell field in the study of each indicated species.

In prior art studies of T-cells and B-cells their differentiation has involved more complex biochemical preparations and procedures including: 1. Acid phosphatase (enzymes); 2. Non-specific esterase; 3. Fragments of human immunoglobulines (Ig G); 4. Non-metachromatic fluorescent dyes, and 5. SRBC—sheep red blood cell preparations having a useful life of about 14 days, it is the basis for rosette formation for identification of T-cells, and is temperature dependant.

T-lymphocytes are found in 60–80% in peripheral blood and 85–90% in the thoracic duct. These cells are known to be related to allograft rejections and both T-cells and B-cells are important considerations in immunology and pathology. B-cells are fewer in number and are from 10–30% in germinal center and medullary cords.

Drug addicts show significant reduction in T-cells.

The vast majority of congenital immunological disorders have relation to T-cell and B-cell systems. Neoplastic diseases are also known to involve the immunogenetic system and patients are recognized to have abnormalities of T-lymphocyte and B-lymphocyte systems. Adult lymphomas are most often of B-cell origin. Childhood lymphomas, on the other hand, bear T-cell markers believed to relate to the more active thymus in early childhood.

Chronic lymphocytic leukemia is a B-cell related, leukemic cells are B-cells and none are known to have T-cell clusters. From the foregoing brief notation, the importance of ready identification, comparison and enumeration of these cells has far reaching significance.

The term metachromatic believed first used by Ehrlich (1897) describes a stain which changes apparent color when sorbed by certain cells. The dye is said to exhibit metachromasia and has been observed as a property of relatively few pure dyes, chiefly basic cationic dyes including methines, polymethines and carbocyanines which color tissue elements in a different color. Metachromasia is also defined as the assumption of different color spectra by different substances when stained by the same dye. Fluorescent metachromasia is very rare. In cytology as here, metachromatic granules or other cell elements are those which assume a color different from that of the dye used to stain them.

Inherent in the above discussion of the terms metachromatic and metachromasia, two factors are involved. One is the biological cell (and its specialized part), which has been called "metachromatic" or "chromotropic" and is a quality or character of the biological cell specimen, and the other is the quality of the dye. Very few dyes possess whatever quality is essential to stimulate structure(s) within a cell to exhibit metachromasia under absorbance as well as fluorescent modes. Conn (9th Edition) reports "pure dyes showing this reaction are few in number". Few reports found indicate that the phenomena has heretofore involved more than two distinct color spectra. In one instance "a light green-blue nuclear stain with a violet metachromasia for cartilage" was reported. However, with stains being normally applied to fixed tissues whose chemical and physical nature is altered by the usual prestaining preparatory procedures, essential cooperation between the character of the natural biological structures within a cell specimen (may be thereby altered and rendered not sensitive to what might otherwise react) so that dye sorption does not occur.

Fluorescent dyestuffs are well known. In fluorescence, more light energy is emitted over select narrow frequencies than is absorbed in these select frequencies, although the total light reflected is not more than the total light absorbed. Fluorescent metachromasia is known (certain dyes in the acridine chromophore class may be metachromatically fluorescent). The term was so used in the Parent application to conform with the term as found in Conn (9th Edition), and Gurr's in "Synthetic Dyes in Biology, Medicine and Chemistry" and Gurr's "Rational use of Dyes in Biology" where no references to "Fluorescent metachromasia" have been noted. In this continuation-in-part application it has been found that a few unusual dyes disclosed in the Parent application are dually metachromatic and these are specific to this disclosure.

Of greatest interest and of most promise as a class are the methine, polymethine, quinoline and carbocyanine dyes where the so identified chromophoric group bridges between other chromophoric groups in the cationic class. Often, for example, a methine or polymethine group is found to bridge between one or more quinoline bearing chromophores.

Subsequent to the filing of the Parent application where basic orange #21, a polymethine dye, was first found to be promising for the purposes of white blood cell classification, samples of other basic orange dyes, identified in the Color Index, namely: basic oranges numbered 22, 27, 42, 44 and 46 were found and checked for metachromasia. The foregoing were dyes reported to be in the polymethine class. Basic oranges 24, 25, 26 and 28 were also tested. The latter were not polymethines. Of all the basic oranges tested including methine and polymethine basic oranges, only basic orange #21 dye was of utility for the purposes herein disclosed.

Basic red 13 and basic violet 16, of the methine and polymethine chromophore class as originally disclosed in the Parent case have been established as bi-modally metachromatically valuable for monocyte blood cell identification hereunder. The search has been extended to cover similarly identified and available methine and polymethine reds and violets of the Color Index.

Basic reds 14, 15, 27, 37, 68 and 102 upon trail testing were found to lack that quality of metachromasia essential to stain monocytes and/or other leukocytes (by absorbance).

However, basic reds 36 and 49 (all polymethines) established as useful for differential metachromatic staining of white blood cells in the first continuation-in-part application also have use here. Basic violet (dyes) 7, 15, 16, 39 and 40 (again all polymethines) were also found useful and operative. However, basic violet 14, not classed as a polymethine in the Color Index, developed no metachromasia in dyeing white blood cells under absorbance or emissive energy.

Having described the best mode presently known to practice the disclosed invention, what is claimed is:

1. In analysis of human blood cells present in a donor specimen in a fixative-free aqueous environment under influence of a fluorescent light emissive energy source, the improvement in identification, enumeration and study of monocytes present in said specimen which comprises staining said specimen with an aqueous solution of a basic, cationic, quaternary organic dyestuff selected from the group consisting of basic orange #21, basic red #13, basic red #36, basic red #49, basic violet #7, basic violet #15, basic violet #16 basic violet #36, basic violet #39 basic violet #40 and carboeyanine; K-5 subjecting said dye stained specimen to emissive wave energy to thereby stimulate fluorescence of said dye exposed cells, emitted fluorescence light providing means for differentiation of monocytes present in the specimen from all other blood cells.

2. In analysis of human blood leukocytes and lymphocytes and the developmental stages of neutrophilic granulocytic cells present in a donor specimen in a fixative-free aqueous environment under influence of a fluorescent light emissive energy source, the improvement in differentiation of each of the individual cell species present into recognizable enumeratable cell species which comprises staining said specimen with an aqueous solution of basic orange #21, subjectingg said dye-stained specimen to emissive wave energy stimulating fluorescence of said dye exposed cells, thereby effecting means for differentiation of each of the cells present in the specimen into cell species identifiable each one from the others.

3. The method of claim 2, where the fluorescent light emissive energy stimulation originates, at least in part, from the coherent light of a laser beam.

4. The method of claim 2, wherein the essential blood cell differentiation method is effected by means of an automatic leukocyte counting means capable of bi-modal wave energy impact on the dyed microscopic field comprising the cells being subjected to analysis and means for observing the said same field under each modal impact means.

5. A method of supervital analysis of human normal or pathologic blood cells present in a donor specimen in an aqueous fixative free environment which comprises exposing said specimen (a) to the dyestuff basic orange #21, (b) stimulating fluorescence of each of the stained species present in said specimen by impact of wave energy and differentiating each of the said blood cells one from the other by the presence or absence of characteristic fluorescent color and pattern of the nucleus and cytoplasm and by the number, size, arrangement, pattern and fluorescent color or quanta of light energy intensities emitted by the granules present, their size, number and locus of the granules in the cytoplasm, if present.

6. A comparative method of supervital analysis of human normal or pathologic blood cells present in a donor specimen including one or more of the following species; myeloblasts, promyelocytes, myelocytes, metamyelocytes platelets, bands, neutrophils, eosinophils, lymphocytes, basophils, monocytes, B-lymphocytes and T-lymphocytes, each one thereof present having been made optically identifiable one from the other by separate selective exposure both to white light absorbance and fluorescent light emission thereby verifying identification of species from the foregoing listed cells present by optical patterns characteristic of said species and by the different quanta of energy reflected and/or emitted from the nucleus, cytoplasm and granules of said blood cells as observed under the foregoing bi-modal light effects.

7. A method of microscopic analysis under bi-modal light sources as described in claim 6, where one healthy normal donor specimen is examined comparatively with a second donor specimen having a suspected pathological origin to provide diagnostic information.

8. A method of fixative-free, supravital human blood cell analysis whereby optical differentiation, comparison and enumeration are made possible of T-lymphocytes and B-lymphocytes present in a donor specimen which comprises metachromatic staining of said specimen in a fixative-free aqueous environment with basic orange #21 dye, subjecting said dyed specimen to a fluorescent light stimulating energy source and thereby differentiating T-cells present from B-cells by a cluster of bright yellow fluorescent granules in the cytoplasm of the T-cells, which may show some fluorescent dull green coloration of the nucleus, and B-cells present whose cytoplasm is essentially free from any fluorescent granules and/or fluorescent color but the nucleus of which does exhibit dull green fluorescence thereby providing required identification.

9. A method of identifying, differentiating and enumerating dye responsive cells in a human blood specimen which comprises staining the specimen in a fixative-free aqueous environment which basic orange #21 dye, subjecting the dyed specimen to fluorescent light emissive wave energy to stimulate fluorescent light emissions from said dye responsive cells, each of said cells emitting quanta of fluorescent light energy of hue, value, chroma and intensity which provides identifying means for differentiation and enumeration of each one of said dye responsive cells.

10. The method of claim 9 wherein the dye responsive cells present in said human blood specimen include one or more of the following species: myeloblasts, promyelocytes, myelocytes, metamyelocytes, platelets, bands, lymphocytes including B-cells and T-cells, basophils, neutrophils, eosinophils or monocytes.

11. A method of supravital human blood analysis whereby optical differentiation, enumeration and comparison of each of the individuals in a granulocytic myeloid series including, when present; promyelocytes, myelocytes, metamyelocytes, bands or neutrophils is achieved by metachromatically staining at least one supravital, fixative free human blood specimen fraction by contact in an aqueous environment with a basic orange #21 dye solution, thereby differentiating the promyelocytes by fluorescent bright yellow primary granules on one side area of the cytoplasm; myelocytes by a relatively even distribution of bright yellow primary granules throughout the cytoplasm; metamyelocytes by a smaller mass of fluorescent bright yellow primary granules in the smaller crescent opposite an unstained clear protrusion of cytoplasm inwardly into the nucleus; the bands by a relatively small cluster of primary bright yellow fluorescent granules in a dominant field of cytoplasm and generally bifurcating the mass of the nucleus; and the neutrophils by a less distinct cytoplasm exhibiting a deep green fluorescence in which the rare granules present fluoresce bright yellow, each member of the foregoing series having an apparently decreasing proportionate cell volume of the nucleus remaining substantially unstained, the first three members of the series having a generally larger over all cell volume cell size than the last two members of the series.

12. In analysis of human blood cells present in a donor specimen in a fixative-free aqueous environment under influence of a fluorescent light emissive energy source. the improvement in identification, enumeration and study of each one or more of the individual cell species present in said specimen; said blood cell species present from the group consisting of myeloblasts, promyelocytes, myelocytes, metamyelocytes, platelets, bands, neutrophils, eosinophils, lymphocytes, basophils, monocytes, B-lymphocytes and T-lymphocytes; which comprises staining said specimen with an aqueous solution of basic orange #21, subjecting said dye-stained specimen to emissive wave energy stimulating fluorescence of said dye exposed cells, thereby effecting means for differentiation of each one of the aforementioned cell species present in the blood specimen from all other cells.

13. The method of supravital human blood cell analysis of claim 12 wherein a band cell containing specimen is subjected to a fluorescent light stimulating energy source, whereby said band cells are differentiated from all other blood-related cells by a relatively small cluster of bright yellow fluorescent granules in portions of the cytoplasm which in pattern substantially bifurcates the central portion of the substantially color free nucleus.

* * * * *